United States Patent [19]

Jordan et al.

[11] Patent Number: 4,749,783

[45] Date of Patent: Jun. 7, 1988

[54] VIRAL INACTIVATION AND PURIFICATION OF ACTIVE PROTEINS

[75] Inventors: Robert E. Jordan, Walnut Creek; Jaleh Kilpatrick, Orinda, both of Calif.

[73] Assignee: Miles Laboratories, Inc., Elkhart, Ind.

[21] Appl. No.: 884,446

[22] Filed: Jul. 11, 1986

[51] Int. Cl.$^4$ .................. A61K 34/14; A61K 37/475
[52] U.S. Cl. .................... 530/393; 530/412; 530/413; 530/414; 530/415; 530/427
[58] Field of Search ............. 530/393, 412, 413, 414, 530/415, 427

[56] References Cited

U.S. PATENT DOCUMENTS

| | | | |
|---|---|---|---|
| 4,265,924 | 5/1981 | Buhler et al. | 530/414 |
| 4,377,514 | 3/1983 | Rubenstroth-Bauer et al. | 530/427 |
| 4,446,134 | 5/1984 | Naito et al. | 530/427 |
| 4,673,733 | 6/1987 | Chandra et al. | 530/412 |

*Primary Examiner*—Delbert R. Phillips
*Assistant Examiner*—Nathan M. Nutter
*Attorney, Agent, or Firm*—James A. Giblin

[57] ABSTRACT

Preparation of active therapeutic proteins comprising two essential steps. In the first step an active protein source is treated under conditions sufficient to inactivate any viruses present (e.g. via heat or chemical treatment). In the second step, the treated active protein source of moderate purity is then treated under conditions sufficient to remove impurities as well as denatured (once active) proteins resulting from the viral inactivation step. In an illustrative embodiment, a biologically active protein such as antithrombin is treated under conditions sufficient to assure viral inactivation and minimal antithrombin deactivation. After the viral inactivation, the antithrombin is contacted with immobilized heparin to complex only the active antithrombin which is then eluted by known means and processed further (e.g., to include desired excipients and then freeze dried). The preferred resulting concentrate is characterized by a high degree of purity, virus inactivation, and absence of denatured or inactive protein (generally less than about 10% by weight inactive form or, in the case of antithrombin, less than about 10% as determined, for example, by crossed immunoelectrophoresis).

24 Claims, No Drawings

VIRAL INACTIVATION AND PURIFICATION OF ACTIVE PROTEINS

BACKGROUND OF THE INVENTION

Field

This disclosure is generally with the purification of safe and efficacious active protein products in which a viral inactivation step precedes a final active protein purification step. By reversing the conventional sequence of steps of purification followed by viral deactivation, it is possible to remove inactive or denatured protein resulting from the relatively harsh conditions of the viral inactivation step. The invention is illustrated with a specific active protein known as antithrombin. As described below, however (the disclosed method is applicable to other biologically active proteins.

Antithrombin, also known as antithrombin III, AT-III or heparin cofactor, is a plasma protein with the ability to inhibit the clotting process. Antithrombin is an inhibitor of coagulation proteases whose inhibitory activity is markedly enhanced in the presence of heparin. Heparin is a sulfated glycosaminoglycan of animal origin widely used as a clinical anticoagulant.

Individuals who lack normal circulating levels of antithrombin in their blood plasma have been shown to be at increased risk of thrombosis. Deficiency states may be either hereditary or acquired. Antithrombin levels below 70% of that of pooled normal plasma are associated with thrombotic risk. Replacement therapy with purified plasma-derived antithrombin may be of considerable benefit to individuals with such deficiencies.

The enhancement of antithrombin activity by heparin is due primarily to a binding interaction between heparin and the inhibitor. The recognition of the tight and highly specific nature of this binding interaction prompted the use of immobilized heparin as an affinity support for the adsorption of antithrombin from biological fluids. See U.S. Pat. No. 3,842,061 to Anderson et al. This technique has been shown by numerous investigators to be a highly-effective step for achieving significant purification of antithrombin. Virtually all large-scale processes for the isolation of antithrombin therefore employ affinity adsorption on immobilized heparin. Other examples of antithrombin purification are well known.

However, the use of heparin affinity chromatography for direct adsorption of antithrombin from plasma at an early point in the commercial Cohn cold ethanol process is complicated for several reasons. Plasma is a highly complex mixture of proteins and other components with varying affinities for heparin. Direct contact of immobilized heparin supports with plasma results in the adsorption of many of these components. Since several different protein products are obtained from the same source plasma, serious regulatory concerns exist regarding the potential for introducing deleterious changes in these products as a result of the affinity contact step.

The adsorption of multiple plasma components on the affinity gel also requires the selective desorption of undesired contaminants before elution of the antithrombin itself. This has proved to be quite difficult to accomplish in a single affinity chromatography step and often requires the inclusion of additional purification steps to remove these contaminants. Alternatively, inclusion of extensive wash steps prior to elution of antithrombin from the heparin gel may increase purity to acceptable levels but only at a considerable cost of antithrombin yield.

Because of the large volumes usually employed during commercial plasma fractionation and the possible impact of chromatography steps on products derived from later steps of the processing, unused waste fractions of the processing have been considered as a source of antithrombin. In particular, plasma source Cohn Fraction IV-1, a normally discarded precipitate deriving from an intermediate step prior to albumin purification, has been found to be a rich source of antithrombin. See Wickerhauser et al, Vox Sang. 36, 281–293 (1979). Such a source, however, provides a non-ideal solution for chromatography (after resuspension) due to the presence of large amounts of lipoproteins and other denatured components. It is usually very difficult to obtain high levels of antithrombin purity by direct chromatography of Fraction IV-1 solutions on immobilized heparin without large sacrifices of yield.

An additional consideration for the purification of any protein from pooled blood plasma or other sources for biologically active proteins is the possibility of viral contamination. Hepatitis B virus and AIDS virus are of particular concern. With regard to Hepatitis B, it was shown that heating at 60° C. for 10 hours in the presence of 0.5M sodium citrate resulted in the complete inactivation of the virus. See Tabor et al, Thrombosis Research 22, 233–238 (1981). The majority of antithrombin activity is maintained during this heat treatment although significant and varying amounts of inactivation have been observed to occur. See Tabor et al, above, and Barrowcliffe et al, Fr. J. Haematology, 55, 37–46 (1983). Thus, the need to insure safety from virus contamination is accompanied by some risk of causing the inactivation of antithrombin itself. This latter possibility is troublesome since the injection of heat-denatured proteins may elicit a response in the patient due to the potentially neo-antigenic nature of these materials.

Until now large scale preparation methods for clinical antithrombin concentrates have incorporated a pasteurization step subsequent to the affinity adsorption step on immobilized heparin. Thus, these products potentially contain large amounts of denatured antithrombin as shown by Barrowcliffe et al, above. We are unaware of methods of preparing biologically active protein products in which denatured or inactive proteins and other impurities are removed subsequent to a viral inactivation step.

SUMMARY OF THE INVENTION

We describe here a method for purification of biologically active proteins which addresses each of the above concerns. This method is thought to be applicable for many active therapeutic proteins. As illustrated below, we show our method is particularly suited for the isolation of antithrombin from a mixture of plasma proteins such as Cohn Fraction IV-1. The essential components of the procedure involve two separate steps: an initial viral inactivation (e.g. pasteurization) step and a subsequent biologically active protein separation step. In the illustrative case of antithrombin, a partially purified antithrombin concentrate is subjected to a viral inactivation step (e.g. pasteurization in the presence of 0.5M sodium citrate as previously described, for example, by Tabor et al, above). The heat-treated antithrombin solution is then separated, e.g., chromatographed directly on a heparin affinity gel (immobilized heparin). This affinity chromatography step assures removal of most of the contaminants deriving from an initial purification as well as most of the denatured proteins, including inactive antithrombin itself, which resulted from the heat-treatment step. The antithrombin is then eluted and concentrated. The concentrate is then preferrably further processed to include, for example, the desired excipients and freeze-dried. The resulting lyophilized protein (antithrombin) concentrate is characterized by a very high level of purity, a considerable degree of virus safety, and a virtual absence of denatured or inactive antithrombin. Plasma sources for active proteins such as antithrombin are well known. Our preferred source is a solution of a current discard fraction known as Cohn fraction IV-I paste. It is thought that other active proteins such as platelet Factor IV, coagulation Factors II, V, VII, VIII, IX and X, Proteins C and S and proteins (such as antibodies, growth factors alpha-1-PI, and virtually any protein which has a biological affinity that can be exploited for purification) found in plasma or expressed from genetically engineered microorganisms or cell lines can be similarly prepared and made both substantially free of active virus and also substantially free of inactive forms of the protein.

In the case of antithrombin purification, our preferred separation step uses heparin immobilized on a carbohydrate support (e.g. heparin covalently bonded to Sepharose agarose). Using the methods of this disclosure, we have been able to obtain a purified antithrombin product substantially free of active viruses and having an activity of at least about six international units of biologically active antithrombin per mg. of total antithrombin protein.

EXAMPLE I (Antithrombin Preparation)

Cohn Fraction IV-1 paste, 6 kilograms (collected from pooled plasma and stored frozen at −30° C.), was dissolved in a total volume of 50 liters of a buffer consisting of 0.1M tris, 0.02M sodium chloride, pH 8.2. After stirring for 1 hour at 5° C., the solution was warmed to 40° C. and stirring continued for an additional hour. The solution was cooled to 20° C. Heparin-Sepharose gel (an immobilized heparin), 6 kilograms previously equilibrated in 0.02M Tris, 0.15M NaCl, pH 7.8, was then added to the Fr. IV-1 solution and stirred for 20 minutes. The suspension was transferred to a filter funnel and the filtrate Fr. IV-1 solution was collected and saved. The gel was then washed extensively with a buffer consisting of 0.02M Tris, 0.3M NaCl, pH 7.5 until the absorbance of the eluate (280 nm) reached 0.36. Elution of antithrombin was then accomplished by washing the gel with a buffer consisting of 0.02M Tris, 2.0M NaCl, pH 7.5. All material eluting with an absorbance greater than 0.2 (280 nm) was collected as a pool for further processing.

The pooled eluate from the batch heparin-Sepharose adsorption was then concentrated in a hollow fiber ultrafiltration device (Romicon) to a final volume of 4.0 liters and diafiltered to a final buffer consisting of 0.02M sodium phosphate, 0.15M NaCl, 0.5M sodium citrate, pH 7.5. The solution was then heated in a water-jacketed vessel under conditions sufficient to assure viral inactivation (e.g., for 10 hours at a solution temperature of 60°±0.5° C.).

Following the heat treatment, the solution was cooled to 20° C. and filtered through a 0.2 micron filter to remove any particulate material resulting from the pasteurization. The filtered solution, including a rinse of the filter apparatus, was then applied directly on a heparin Sepharose column (14×21 cm) previously equilibrated with a buffer consisting of 0.02M sodium phosphate, 0.15M NaCl pH 7.5 and the column was washed with this same buffer following sample application. The absorbance of the eluate solution was monitored (280 nm) until a baseline level was reached and the column was then eluted with phosphate buffer containing 2M NaCl. All material eluting with an absorbance greater than 0.04 was collected as a pool with a total volume of 3.05 liters. A summary of antithrombin recoveries is presented in the Table below.

TABLE

Purification of antithrombin from 6 kilograms of Fraction IV-1

| Step | volume (liters) | A280 | antithrombin units/ml | anti-thrombin tot. units | antithrombin spec. act. units/ A280 | yield |
|---|---|---|---|---|---|---|
| Fr. IV-1 suspension | 50 | 38.6 | 1.2 | 60,000 | 0.03 | 100% |
| Heparin-Sepharose batch eluate | 4.0 | 1.23 | 9.0 | 36,000 | 7.32 | 60% |
| Pasteurized eluate | 4.5 | 1.0 | 6.25 | 28,125 | 6.25 | 47% |
| Eluate from heparin-Seph chromatography | 3.05 | 0.98 | 8.5 | 25,925 | 8.67 | 43% |

EXAMPLE II

The steps of Example I except that the final pasteurized antithrombin product was subsequently lyophilized with an amino acid (0.1M alanine) as a stabilizer.

EXAMPLE III

The steps of Example I, but with an additional wash of the heparin-agarose gel following batch-wise contact of the Fraction IV-1 solution with a buffer containing 0.02M TRIS, 0.15M NaCl and 1-2gr. dextran sulfate per liter, pH 7.5.

Although the above Examples describe the viral inactivation and purification of a very specific active protein, antithrombin, it should be kept in mind that the disclosed technique should be applicable to a wide variety of active proteins obtained from a variety of sources (e.g. animal or human plasma, genetically engineered microorganisms and cell lines, etc.). The main requirements for employing the disclosed techniques are two fold: (1) viral inactivation in a biologically active protein product, and (2) an active protein product having minimal, if any, denatured or inactive form of the active protein.

Examples of viral inactivation techniques that can be used are pasteurization, chemical treatment (e.g. using agents such as copper phenanthroline as in U.S. Pat. No. 4,534,972, etc.) and irradiation. Examples of active protein separation techniques include methods which will allow separation based on the biological activity of the protein so that there is a discrimination between active and inactive forms (e.g. affinity chromatography or any use of a specific binding agent such as an antibody which recognizes a biologically active form of the protein).

As used herein, the term biologically active, when applied to proteins, means that form or configuration of the protein in which the protein demonstrates its intended function or is useful for an intended result (as opposed to the same protein in an inactive, denatured or useless state). Whether a given protein possesses biological activity to demonstrate its intended function or accomplish an intended result can be determined by means known to those skilled in the art (e.g. simple functional activity assays, immunologically, etc.).

Viral inactivation or substantially free of active viruses means removal or inactivation of any viruses present to a safely acceptable or non-detectable level. A pasteurized form of a given active protein preparation means a preparation that has been subjected to pasteurization or a heat treatment sufficient to inactivate any viruses present (e.g. heating at 60° C. for at least about 10 hours). Free of denatured or inactive forms of a given protein means that a given protein product comprises mainly of biologically active forms of the protein and the denatured or inactive form is absent or present in undetectable or minimal amounts (e.g., less than about 10% by weight generally or, in the case of antithrombin, the inactive species of the antithrombin is less than about 10%, as determined by crossed immunoelectrophoresis).

Given the above disclosure, it is thought variations will occur to those skilled in the art. Accordingly, it is intended that the above example should be construed as illustrative and the scope of the invention should be limited only by the following claims.

We claim:

1. A method of preparing a biologically active, therapeutic protein product substantially free of active viruses comprising the steps of:
   (a) subjecting a source for a given biologically active protein to a viral inactivation step under conditions sufficient to inactivate any virus present, and
   (b) subjecting the product of step (a) to a protein separation step under conditions sufficient to remove biologically inactive forms of the protein so that the inactive forms comprise less than about 10% by weight of the total protein.

2. The method of claim 1 wherein the biologically active protein is selected from a plasma protein and a protein derived from a microorganism or cell line capable of expressing the protein.

3. The method of claim 1 wherein the product of step (a) is pasteurized under conditions sufficient to assure inactivation of any viruses present in the solution.

4. The method of claim 3 wherein the pasteurization step comprises heating the solution at a temperature of at least about 60° C. for at least about 10 hours.

5. The method of claim 1 wherein the protein is antithrombin.

6. The method of claim 5 wherein the separation of step (b) comprises contacting a solution of the product with immobilized heparin.

7. The method of claim 6 wherein the immobilized heparin comprises heparin bonded to a carbohydrate support material.

8. A method of preparing antithrombin from a human plasma solution or derivative human plasma fraction comprising the steps of (a) contacting the solution with immobilized heparin under conditions sufficient to complex antithrombin present in the solution; (b) eluting the antithrombin from the immobilized heparin to form a solution of antithrombin; (c) pasteurizing the solution of step (b); (d) contacting the solution of step (c) with immobilized heparin under conditions sufficient to complex the antithrombin with the immobilized heparin; and (e) eluting the antithrombin from the immobilized heparin of step (d).

9. The method of claim 8 wherein the solution of step (b) is pasteurized under conditions sufficient to assure inactivation of any viruses present in the solution.

10. The method of claim 9 wherein the pasteurization step comprises heating the solution at a temperature of at least about 60° C. for at least about 10 hours.

11. The method of claim 8 wherein the separation of step (a) is a batch-type contact and the contact of step (d) comprises passing a solution through a column containing the immobilized heparin.

12. The method of claim 8 wherein the immobilized heparin comprises heparin bonded to a carbohydrate support material.

13. The method of claim 8 wherein the antithrombin is purified from a derivative human plasma fraction known as Cohn Fraction IV-1 paste.

14. A highly purified antithrombin preparation comprising active antithrombin substantially free of active viruses, substantially free of deactivated antithrombin and having an activity of at least about 6 international units of active antithrombin per mg. of total antithrombin protein.

15. The preparation of claim 8 in lyophilized form including an alanine stabilizer.

16. The preparation of claim 15 which includes an alanine stabilizer.

17. The preparation of claim 8 in a pharmaceutically acceptable form.

18. The preparation of claim 14 in pasteurized form.

19. A method of preparing biologically active antithrombin substantially free of active viruses comprising the steps of:
   (a) subjecting a source of biologically active antithrombin to a viral inactivation step under conditions sufficient to inactivate any virus present, and
   (b) subjecting the product of step (a) to a separation step under conditions sufficient to remove biologically inactive forms of the antithrombin so that the inactive forms of the antithrombin comprise less than about 10% of the total antithrombin, as determined by crossed immunoelectrophoresis.

20. The method of claim 19 wherein the biolgocially active antithrombin is selected from a plasma antithrombin and antithrombin derived from a microorganism or cell line capable of expressing the antithrombin.

21. The method of claim 19 wherein the product of step (a) is pasteurized under conditions sufficient to assure inactivation of any viruses present.

22. The method of claim 21 wherein the pasteurization step comprises heating the antithrombin at a temperature of at least about 60° C. for at least about 10 hours.

23. The method of claim 22 wherein the protein is heated in a solution.

24. The mehtod of claim 9 wherein the separation of step (b) comprises contacting a solution of the antithrombin with immobilized heparin.

* * * * *